(12) United States Patent
Hörold et al.

(10) Patent No.: US 6,855,757 B2
(45) Date of Patent: Feb. 15, 2005

(54) PREPARATION OF GLYCOL CARBOXYETHYLMETHYLPHOSPHINATE

(75) Inventors: Sebastian Hörold, Erftstadt (DE); Heinz-Peter Breuer, Hürth (DE); Elisabeth Jung, Bedburg (DE)

(73) Assignee: Clariant GmbH, Frankfurt (DE)

( * ) Notice: Subject to any disclaimer, the term of this patent is extended or adjusted under 35 U.S.C. 154(b) by 266 days.

(21) Appl. No.: 10/283,909

(22) Filed: Oct. 30, 2002

(65) Prior Publication Data

US 2003/0171466 A1 Sep. 11, 2003

(30) Foreign Application Priority Data

Nov. 2, 2001 (DE) .......................... 101 53 780

(51) Int. Cl.$^7$ .......................... C08K 5/51; C08G 63/18; C08G 63/19
(52) U.S. Cl. .......................... 524/133; 558/110; 528/308; 528/308.1; 528/308.2; 528/337; 528/400; 252/609
(58) Field of Search .......................... 524/133; 558/110; 528/308, 308.1, 308.2, 337; 252/609

(56) References Cited

U.S. PATENT DOCUMENTS

| | | | |
|---|---|---|---|
| 4,022,826 A | 5/1977 | Lohmar et al. | 260/543 |
| 4,062,888 A | 12/1977 | Ohorodnik et al. | 260/545 |
| 5,399,428 A | 3/1995 | Asrar | 428/364 |
| 6,090,967 A | 7/2000 | Horold et al. | 558/105 |
| 6,909,968 | 7/2000 | Horold et al. | 558/137 |

FOREIGN PATENT DOCUMENTS

| | | |
|---|---|---|
| DE | 25 29 731 | 12/1976 |
| DE | 25 40 283 | 3/1977 |
| DE | 39 40 713 | 6/1991 |
| EP | 0 432 620 | 6/1991 |
| EP | 0 969 008 | 1/2000 |
| EP | 0 969 009 | 1/2000 |
| GB | 1 517 865 | 7/1978 |

OTHER PUBLICATIONS

English abstract for DE 3940713, Jun. 13, 1991.
Khairullin, T.I., et al., Zh Obshch. Khim., 37, (1967), pp. 710–714.
Houben–Weyl, vol. 12/1, pp. 230–232, 1963.
Houben–Weyl, vol. 12/1, pp. 258–259, 1963.
Houben–Weyl, vol. 12/1, pp. 306, 1963.

*Primary Examiner*—Kriellion A. Sanders
(74) *Attorney, Agent, or Firm*—Anthony A. Bisulca

(57) ABSTRACT

The invention relates to a process of preparing glycol carboxyethylmethylphosphinate, which comprises
  a) reacting elemental yellow phosphorus with methyl chloride in the presence of an alkali or alkaline earth metal hydroxide to form a mixture which includes the alkali and/or alkaline earth metal salts of methylphosphonous, phosphorous and hypophosphorous acids as main constituents,
  b) esterifying the methylphosphonous acid from the mixture obtained by a),
  c) removing the methylphosphonous ester from the mixture,
  d) adding the thus obtained methylphosphonous ester to an acrylic ester,
  e) hydrolyzing the diester thus obtained,
  f) esterifying the resulting carboxyethylmethylphosphinic acid with ethylene glycol directly to the glycol carboxyethylmethylphosphinate.

The invention also relates to the use of the glycol carboxyethylmethylphosphinates prepared according to the invention as reactive flame retardants for polymers.

21 Claims, No Drawings

PREPARATION OF GLYCOL CARBOXYETHYLMETHYLPHOSPHINATE

The present invention relates to a process for preparing glycol carboxyethylmethylphosphinate and also to the use of the products prepared by this process.

Glycol carboxyethylmethylphosphinates are valuable synthons in the manufacture of low-flammability polyester fibers. For instance, DE-A-39 40 713 describes the production of low-flammability synthetic fibers which contain groups of the formula (I) in the polymer chain. Low-flammability synthetic fibers of this type are commercially available as Trevira CS.

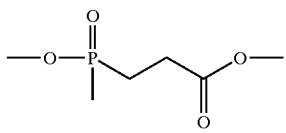

(I)

U.S. Pat. No. 5,399,428 A1 and DE 2 529 731 describe flame-retardant linear polyesters due to incorporation of carboxy-phosphinic acids.

Carboxyl-containing phosphinic acids are obtained when phosphonous dihalides (dihalophosphines) are reacted with activated olefinic compounds such as acrylic or methacrylic acid derivatives for example and subsequently hydrolyzed (Houben-Weyl, Volume 12/1, p. 230; K. K. Khairullin, T. I. Sobchuk, A. N. Pudovik, Zh. Obshch. Khim. 37, 710 (1967)). The hydrolysis with organic acids by-produces the halides of the acids.

Glycol carboxyethylmethylphosphinate can be obtained as described in U.S. Pat. No. 4,062,888, Hoechst A G (1977), by reaction of methyldichlorophosphine with acrylic acid, subsequent formation of the intramolecular anhydride and esterification with ethylene glycol (Figure 1).

The aforementioned methyldichlorophosphine has itself hitherto been prepared in a costly and inconvenient synthesis from phosphorus trichloride and imethyl chloride in the presence of aluminum chloride (Houben-Weyl, Volume 12/1, p. 306). The reaction is strongly exothermic and difficult to control on a commercial scale. In addition, it gives rise to various by-products which, like in part the aforementioned starting materials too, are toxic and/or corrosive and hence extremely undesirable.

In addition, phosphonous dihalides can be reacted with alkyl halides in the presence of aluminum chloride (Houben-Weyl, Volume 12/1, p. 232).

Phosphinic esters can also be prepared from dialkyl phosphonites by Michaelis-Arbuzov reaction. Dialkyl phosphonites are in turn prepared from phosphonous dihalides and hydroxy compounds.

DE 25 40 283 A1 describes the preparation of carboxyl-containing organic phosphorus compounds by addition of phosphines to α,β-unsaturated carboxylic acids in the presence of aqueous hydrochloric acid and subsequent oxidation.

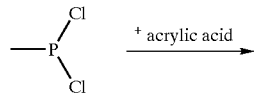

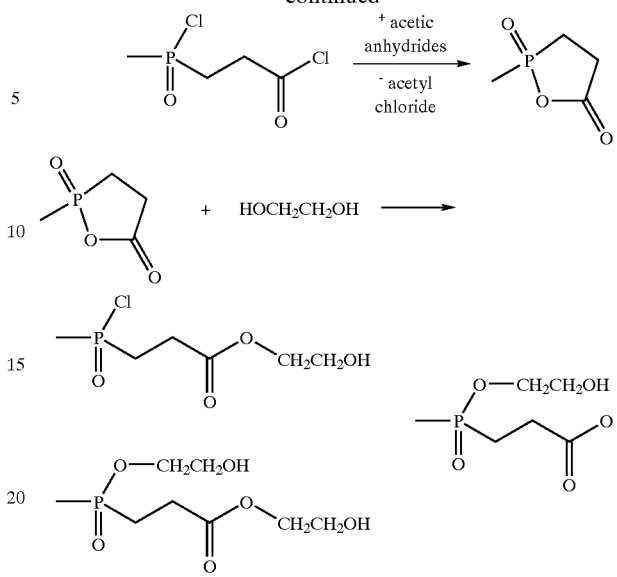

Preparation of glycol carboxyethylmethylphosphinate according to U.S. Pat. No. 4,062,888 or DE 2 529 731

Phosphinic esters are obtained when phosphonous monoesters are added to 1-olefins in the presence of peroxidic catalysts but the yields are low. The addition of phosphonous monoesters to activated double bonds in the presence of an alkoxide catalyst works better. Useful unsaturated compounds include α,β-unsaturated carboxylic esters, α,β unsaturated carbonitriles, α,β unsaturated ketones and also alkyl vinyl sulfones and vinyl acetate (Houben-Weyl, Volume 12/1, p. 258–259).

Phosphonous monoesters themselves are prepared from phosphonous dihalides by reaction with alcohols or by hydrolysis and subsequent esterification.

There is therefore a need for processes for preparing glycol carboxyethylmethylphosphinate that is simple to carry out and which provides unitary products in high yield. Such a process shall also be environmentally distinctly superior to prior art processes.

It is an object of the present invention to provide a process for preparing glycol carboxyethylmethylphosphinate that avoids the aforementioned disadvantages and starts from elemental yellow phosphorus as a reactant.

This object is achieved by a process of the kind described at the outset, which comprises a) reacting elemental yellow phosphorus with methyl chloride in the presence of an alkali or alkaline earth metal hydroxide to form a mixture which includes the alkali and/or alkaline earth metal salts of methylphosphonous, phosphorous and hypophosphorous acids as main constituents, b) esterifying the methylphosphonous acid in the mixture obtained by a), c) removing the methylphosphonous ester from the mixture, d) adding the thus obtained methylphosphonous ester to an acrylic ester, e) hydrolyzing the diester thus obtained, f) esterifying the resulting carboxyethylmethylphosphinic acid with ethylene glycol directly to the glycol carboxyethylmethylphosphinate.

The process of the invention has appreciable advantages over prior art processes in that, for example, it obviates phosphonous dihalide reactants and has a positive balance in product distribution too.

The reaction in step a) is preferably carried out in a two-phase system composed of aqueous alkali or alkaline earth metal hydroxide or mixtures thereof and an organic solvent.

The organic solvent used preferably comprises straight-chain or branched alkanes, alkyl-substituted aromatic solvents, water-immiscible or only partly water-miscible alcohols or ethers used alone or combined with each other.

The organic solvent used is more preferably toluene, alone or in combination with alcohols.

The reaction (step a) is preferably carried out in the presence of a phase transfer catalyst.

The phase transfer catalyst preferably comprises tetraalkylphosphonium halides, triphenylalkylphosphonium halides or tetraorganoammonium halides.

The temperature in the course of the reaction of step a) is preferably in the range from −20 to +60° C.

More preferably, the temperature is in the range from 0 to 30° C.

The reaction of step a) is preferably carried out under a pressure in the range from 0 to 10 bar.

In a preferred embodiment of the process according to the invention, the yellow phosphorus is suspended in a solvent or solvent mixture and then reacted with an alkyl halide and a compound of the formula MOH or M'(OH)$_2$ or mixtures thereof, where M is an alkali metal and M' is an alkaline earth metal.

The yellow phosphorus and the methyl chloride are preferably reacted with each other in a molar ratio in the range from 1:1 to 1:3, the molar ratio of yellow phosphorus to compound of the formula MOH or M'(OH)$_2$ being in the range from 1:1 to 1:5.

In step b), the methylphosphonous acid is preferably directly esterified with a linear or branched alcohol of the general formula R—OH, where R is a linear or branched alkyl radical of 1–10 carbon atoms. It is more preferable to use n-butanol, isobutanol or ethylhexanol.

In step c), the ester of methylphosphonous acid is preferably removed by distillation.

The esterification of the phosphonous acid to the corresponding monoester can be achieved for example by reacting with higher boiling alcohols while using azeotropic distillation to remove the water formed.

The adding of step d) is preferably effected in the presence of catalysts.

The catalysts in question are preferably basic catalysts. Alternatively it is also possible to use acids or cationic free-radical initiators.

The basic catalysts are preferably alkali or alkaline earth metal alkoxides.

The acrylic ester of the general formula (II) is preferably an ester of the same alcohol as used to esterify the methylphosphonous acid in step b).

The acrylic ester of the general formula (II) is preferably hydroxyethyl acrylate, methyl acrylate, ethyl acrylate, butyl acrylate or 2-ethylhexyl acrylate.

The invention also provides for the use of the functional phosphinic acids prepared by the process according to the invention as reactive flame retardants for polymers.

The invention also provides for the use of the glycol carboxyethylmethylphosphinates prepared by the process according to the invention as reactive flame retardants for thermoplastic polymers such as polyethylene terephthalate.

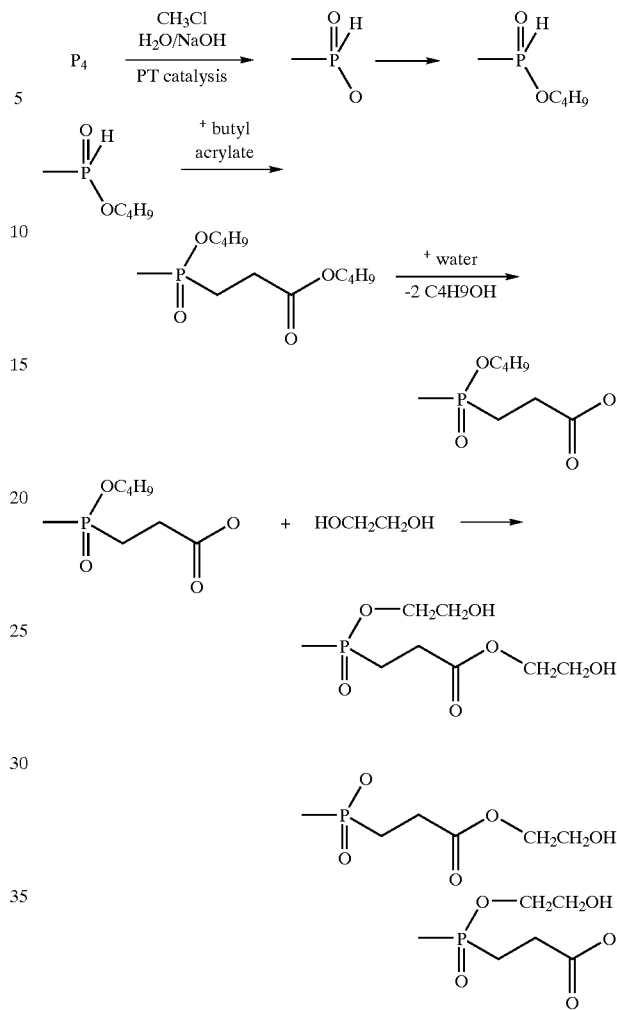

Figure 4F: Formula scheme of inventive progress for preparing glycol carboxyethylmethylphosphinates The examples hereinbelow illustrate the invention.

EXAMPLE 1

Reaction of Yellow Phosphorus with Methyl Chloride

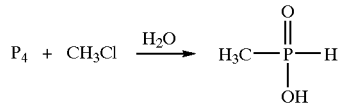

In a 5 l stainless steel pressure reactor, a solution of 26.1 (0.05 mol) of tributylhexadecylphosphonium bromide in 1000 ml of toluene was preheated to 60° C. After 62 g (2 mol) of yellow phosphorus had been added, the mixture was cooled to −10° C. with vigorous stirring and 202 g (4 mol) of methyl chloride were then condensed in. 400 g of 50% aqueous sodium hydroxide solution were then metered in over 2 hours, during which the temperature was maintained at −10° C. 400 g of water were added over an hour, which was followed by stirring for a further hour, warming to room temperature and subsequent decompression of the reactor via combustion. Two homogeneous liquid phases were obtained, which were separated and analyzed.

The aqueous phase (weight: 920 g) contained 65.6 mol % of methylphosphonous acid, 14.9 mol % of phosphorous acid and 13.7 mol % of hypophosphorous acid and 2.8 mol % of dimethylphosphinic acid in the form of their sodium salts and also 3 mol % of dimethyldiphosphine.

Phosphine oxidation/NaCl removal: The solution was admixed with 60 g of 5% aqueous hydrogen peroxide solution, with 240 g of 36% hydrochloric acid and with 400 g of 2-ethylhexanol, added in succession. After the water content had been removed by distillation under a water separator, the precipitated sodium chloride was filtered off and washed with 100 g of 2-ethylhexanol.

EXAMPLE 2

Esterification of Methanephosphonous Acid in the Reaction Mixture

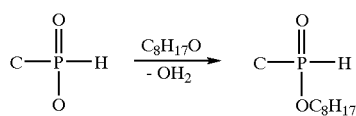

The ethylhexanol solutions of Example 1 were combined and heated at about 120° C. under slightly reduced pressure under a water separator for about 6 hours.
Isolation of the Ester The esterified reaction mixture was subsequently freed of excess ethylhexanol by distillation and subjected to a vacuum distillation. At a pressure of 0.3 mm and a head temperature of 75° C., 220 g of 2-ethylhexyl methanephosphonite passed over. The product is obtained in the form of a clear, colorless liquid in a purity above 99%, corresponding to a yield of 58%, based on the yellow phosphorus used. Analyses: 16.0% of phosphorus (theory: 16.2%); $^{31}$P NMR: doublet at 34 ppm (diastereomer pair).

EXAMPLE 3

Addition of n-butyl Methanephosphonite Onto Butyl Acrylate

A 500 ml five-neck flask fitted with thermometer, reflux condenser, high-speed stirrer and dropping funnel is charged with 136 g (1 mol) of n-butyl methanephosphonite and 128 g (1 mol) of butyl acrylate. 5 ml of sodium butoxide (30%) are added dropwise to the stirred mixture at such a rate that a reaction temperature of max. 120° C. ensues. The mixture is subsequently allowed to react at 80° C. for a further 10 min. A pale yellow liquid is obtained.

$^{31}$P NMR (CHCl$_3$): 56 ppm

The dibutyl ester thus obtained is distilled at 130° C. and 0.5 mm vacuum.

EXAMPLE 4

Hydrolysis of Dibutyl Carboxyethylmethylphosphinate
528 g (2 mol) of the dibutyl carboxyethylmethylphosphinate obtained according to Example 4 are charged to a 1 l five-neck flask fitted with thermometer, reflux condenser, high-speed stirrer and dropping funnel. At 160° C., 500 ml of water are metered in over 4 h and a butanol-water mixture is distilled off. 281 g of butanol are obtained, which corresponds to 95% of theory. The distillatively removed butanol is re-used to esterify the methylphosphonous acid. 300 g of carboxyethylmethylphosphinic acid are obtained as a white solid having a melting point of about 95° C. and a $^{31}$P NMR purity of >97%.

EXAMPLE 5

Esterification of Carboxyethylmethylphosphinic Acid with Ethylene Glycol 445.8 g of carboxyethylmethylphosphinic acid (2.93 mol) according to Example 5 are dissolved in 356.4 g of ethylene glycol (5.86 mol) at 90° C. A clear solution is obtained, which is stable in storage.

The water formed in the course of the esterification is removed at 160° C. in a 1 l three-neck flask fitted with thermometer, stillhead, distillation column and high-speed stirrer. The 54 g of distillate obtained after 2 h is 100% water. The water quantity corresponds to a diester formation to 52.4% of theory. The phosphorus content of the product is 12.4% and includes free ethylene glycol. The color number (Hazen) is 30, the Berger whiteness is 75%, the yellowness is 5%, the saponification number is 420 mg of KOH/g and the water content (Karl Fischer titration) is 0.1%.

The product thus obtained can be used for manufacturing low-flammability polyester fibers.

What is claimed is:
1. A process of preparing glycol carboxyethylmethylphosphinate, comprising the steps of:
   a) reacting elemental yellow phosphorus with methyl chloride in the presence of an alkali or alkaline earth metal hydroxide to form a mixture which includes the alkali and/or alkaline earth metal salts of methylphosphonous, phosphorous and hypophosphorous acids as main constituents,
   b) esterifying the methylphosphonous acid from the mixture obtained by a),
   c) removing the methylphosphonous ester from the mixture,
   d) adding the thus obtained methylphosphonous ester to an acrylic ester,
   e) hydrolyzing the diester thus obtained,
   f) esterifying the resulting carboxyethylmethylphosphinic acid with ethylene glycol directly to the glycol carboxyethylmethylphosphinate.
2. The process of claim 1, wherein step a) is carried out in an organic solvent.
3. The process of claim 2, wherein the organic solvent is selected from the group consisting of straight-chain or branched alkanes, alkyl-substituted aromatic solvents, water-immiscible or only partly water-miscible alcohols and ethers used alone or combined with each other.
4. The process of claim 2, wherein the organic solvent used is toluene, alone or in combination with alcohols.
5. The process of claim 1, wherein step a) is carried out in the presence of a phase transfer catalyst.
6. The process of claim 5, wherein the phase transfer catalyst comprises tetraalkylphosphonium halides, triphenylalkylphosphonium halides or tetraorganoammonium halides.
7. The process of claim 1, wherein step a) is carried out at a temperature in the range from −20 to +60° C.
8. The process of claim 1, wherein step a) is carried out at a temperature in the range from 0 to 30° C.
9. The process of claim 1, wherein step a) is carried out under a pressure in the range from 0 to 10 bar.
10. The process of claim 1, wherein step a) further comprises suspending the yellow phosphorus in a solvent or solvent mixture and then reacting with an alkyl halide and a compound of the formula MOH or M'(OH)$_2$ or mixtures thereof, where M is an alkali metal and M' is an alkaline earth metal.

11. The process of claim 10, wherein the yellow phosphorus and the methyl chloride are reacted with each other in a molar ratio in the range from 1:1 to 1:3, the molar ratio of yellow phosphorus to compound of the formula MOH or M'(OH)$_1$ being in the range from 1:1 to 1:5.

12. The process of claim 1, wherein step b) further comprises esterifying the methyl phosphonous acid with an alcohol in a mixture.

13. The process of claim 1, wherein step c) further comprises removing the methanephosphonous ester by distillation.

14. The process of claim 1, wherein step d) is effected in the presence of a catalyst.

15. The process of claim 14, wherein the catalyst is a basic catalyst.

16. The process of claim 14, wherein the basic catalyst is an alkali or alkaline earth metal alkoxide.

17. The process of claim 1, wherein the acrylic ester is methyl acrylate, butyl acrylate or ethylhexyl acrylate.

18. A flame retardant polymer comprising a polymer and glycol carboxyethylmethylphosphinate prepared by the process of claim 1.

19. A reactive flame retardant for a thermoplastic polymer comprising the glycol carboxyethylmethylphosphinate prepared by the process of claim 1, wherein the thermoplastic polymer is selected from the group consisting of polyethylene terephthalate, polybutylene terephthalate or polyamide.

20. A process for making a flame retardant polymer comprising the step of adding to the polymer the glycol carboxyethylmethylphosphinate prepared by the process of claim 1.

21. The process of claim 20, wherein the polymer is selected from the group consisting of polyethylene terephthalate, polybutylene terephthalate or polyamide.

* * * * *